(12) United States Patent
Dhingra et al.

(10) Patent No.: US 8,901,039 B2
(45) Date of Patent: Dec. 2, 2014

(54) USE OF PHOTOSYNTHETIC PIGMENT STABILIZING AGENTS TO REGULATE RIPENING AND QUALITY IN FRUITS AND VEGETABLES

(71) Applicant: Washington State University, Pullman, WA (US)

(72) Inventors: Amit Dhingra, Pullman, WA (US); Scott Schaeffer, Bremerton, WA (US)

(73) Assignee: Washington State University, Pullman, WA (US)

( * ) Notice: Subject to any disclaimer, the term of this patent is extended or adjusted under 35 U.S.C. 154(b) by 0 days.

(21) Appl. No.: 13/826,860

(22) Filed: Mar. 14, 2013

(65) Prior Publication Data
US 2013/0203598 A1 Aug. 8, 2013

Related U.S. Application Data

(63) Continuation-in-part of application No. PCT/US2012/039038, filed on May 23, 2012.

(60) Provisional application No. 61/489,103, filed on May 23, 2011.

(51) Int. Cl.
| | |
|---|---|
| *A01N 37/44* | (2006.01) |
| *A23B 7/154* | (2006.01) |
| *A01N 63/00* | (2006.01) |

(52) U.S. Cl.
CPC ............... *A23B 7/154* (2013.01); *A01N 37/44* (2013.01)
USPC ........... 504/320; 426/321; 514/561; 504/118; 504/147

(58) Field of Classification Search
CPC ....... A23B 7/154; A01N 37/44; A01N 27/00; A01N 31/02; A01N 33/04; A01N 33/08; A01N 33/12; A01N 37/06
USPC ........... 504/320, 118, 147; 514/561; 426/321
See application file for complete search history.

(56) References Cited

U.S. PATENT DOCUMENTS

| | | | |
|---|---|---|---|
| 4,957,757 A | * | 9/1990 | Law et al. ............ 426/281 |
| 5,952,267 A | | 9/1999 | Mottram |
| 5,972,840 A | * | 10/1999 | Mottram ............ 504/244 |
| 7,345,008 B1 | | 3/2008 | Suzuki |
| 2007/0104751 A1 | | 5/2007 | Levar |

FOREIGN PATENT DOCUMENTS

| | | | |
|---|---|---|---|
| CN | 102197827 A | * | 9/2011 |
| EP | 2 036 438 A1 | * | 3/2009 |
| WO | 96/23413 A1 | | 8/1996 |

OTHER PUBLICATIONS

Hurme, Eero U.; Kinnunen, Arvo; Heinio, Raija-Liisa; Ahvenainen, Raija and Jokinen, Kari, "The Storage Life of Packed Shredded Iceberg Lettuce Dipped in Glycine Betaine Solutions", Journal of Food Protection, vol. 62, No. 4, Apr. 1999, pp. 363-367 (Abstract).*
Zhang Hai-ying, Wang You-nian, Han Tao, Li Li-ping and Xu Li, "Effect of Exogenous Glycine Betaine on Chilling Injury and Chilling-Resistance Parameters in Cucumber Fruits Stored at Low Temperature", Scientia Agrī cultura Sinica, 2008,4 1(8):2407-2412.*
Myeong Min Lee, Sun Hi Lee, and Ky Young Park, "Effects of Spermine on Ethylene Biosynthesis in Cut Carnation (*Dianthus caryophyl/us* L.) Flowers During Senescence", Journal of Plant Physiology, vol. 151. pp. 68-73 (1997).*
Leo Winer and Akiva Apelbaum, "Involvement of Polyamines in the Development and Ripening of Avocado Fruits", Journal of Plant Physiology, vol. 126. pp. 223-233 (1986).*
The Old Farmer's Almanac, "Cucumbers", accessed from http://www.almanac.com/plant/cucumbers on Jun. 25, 2014.*
Vera Hershkovitz, Sam I. Saguy and Edna Pesis, "Postharvest application of 1-MCP to improve the quality of various avocado cultivars", Postharvest Biology and Technology 37 (2005) 252-264.*

* cited by examiner

*Primary Examiner* — John Pak
*Assistant Examiner* — Nathan W Schlientz
(74) *Attorney, Agent, or Firm* — Whitham Curtis Christofferson & Cook, PC (57) ABSTRACT

Methods and compositions to temporarily delay the ripening, maturation, senescence and pathogen infection of produce such as fruits, vegetables and ornamental plants are provided. The methods involve the application of a photosynthetic pigment and/or membrane stabilizing chemical (e.g. glycine betaine) to produce which is identified as in need of such delay. Application may be prior to harvest, at or during harvest or post-harvest.

2 Claims, 3 Drawing Sheets

USE OF PHOTOSYNTHETIC PIGMENT STABILIZING AGENTS TO REGULATE RIPENING AND QUALITY IN FRUITS AND VEGETABLES

CROSS-REFERENCE TO RELATED APPLICATIONS

This application claims benefit of U.S. provisional patent application 61/489,103, filed May 23, 2011, and claims benefit of and is a continuation-in-part of International patent application PCT/US12/39038, filed May 23, 2012, the complete contents of both of which are hereby incorporated by reference.

BACKGROUND OF THE INVENTION

1. Field of the Invention

The invention generally relates to methods for delaying the abscission, preharvest drop, ripening, maturation, senescence or pathogen entry of produce such as fruit and vegetables. In particular, the invention provides a method of temporarily preventing or delaying the ripening or maturation of produce by the pre- or post-harvest application of a photosynthetic pigment or membrane stabilizing agent and osmoregulaor such as glycine betaine.

2. Background of the Invention

Postharvest treatment with the synthetic molecule 1-methylcyclopropene (1-MCP) is used by the fruit industry to slow the ripening process of fruit during storage. 1-MCP treatment extends the shelf life of treated fruit, thereby increasing the availability of fresh fruit to consumers throughout much of the year. 1-MCP is structurally related to the natural plant hormone ethylene and slows ripening by binding to ethylene receptors, thereby blocking the binding of ethylene and preventing a ripening response to the hormone. In some cases, over time, the effect of 1-MCP treatment wanes and ripening of the treated commodity can occur. The use of 1-MCP in this manner is described in U.S. Pat. No. 6,017,849, the complete contents of which are hereby incorporated by reference in entirety.

Unfortunately, certain fruits do not respond well to 1-MCP. For example, applications of 1-MCP have had mixed success in pear storage, often yielding pears that are unable to ripen at all after treatment. The resulting pears remain hard and have relatively low levels of soluble sugars, which impair their taste and appeal to consumers. For these and other types of fruit, there is a need in the industry to provide alternative methods for the treatment of fruit to slow the ripening process. It would also be desirable to have available an anti-ripening agent that is a natural product rather than a synthetic such as 1-MCP.

Several attempts to control or delay ripening of fruits and vegetables during transport and storage have been made. For example, U.S. Pat. Nos. 6,124,525, 6,080,914, 5,952,546 and 5,512,466 describe various genetic modifications of plants that may be used to alter the ripening process. However, the use of genetically modified organisms is generally not popular with the public at large, may have far-reaching and unpredictable environmental consequences, and requires a high degree of government regulation.

U.S. Pat. No. 7,943,549 to Pierce et al. describes methods for delaying a plant development process by exposing a plant or plant part to one or more bacteria or enzymes. Bacteria such as *Rhodococcus* spp., *Pseudomonas chloroaphis*, and *Brevibacterium ketoglutamicum* may be used. However, the use of live organisms can be fraught with problems since they are sensitive to environmental conditions, and control of the process (e.g. reversibility) may be difficult. In addition, the public may be reluctant to consume produce that has been "infected" with bacteria.

Glycine betaine is known to be used as an osmolyte regulator when applied to fruit before harvesting so as to prevent or reduce blemishes or damage of the skin of the fruit (e.g. to reduce cherry cracking; see U.S. Pat. No. 5,972,840 to Mottram, the complete contents of which are hereby incorporated by reference). However, U.S. Pat. No. 5,972,840 makes no mention of the use of glycine betaine to forestall ripening or prevent pathogen entry of fruit or other produce.

In addition to its role in ripening, ethylene plays a role in abscission, the process of a plant intentionally shedding an organ. Plants naturally use the process of abscission to drop fruit at the end of a growing season. While this process is beneficial in nature, dropping fruit before harvest leads to large losses in the agricultural world. U.S. Pat. Nos. 5,869,424 and 6,153,559 addresses this issue through the application of aminoethoxyvinylglycine (commercially named RETAIN®) and its precursor N-acetyl aminoethoxyvinylglycine, respectively, to inhibit ethylene biosynthesis. An alternative strategy was described in U.S. patent US 2012/0101164 A1 where application of 1-naphthaleneacetic acid (NAA) also delayed the abscission of fruit. However, these approaches act through different mechanistic properties compared to glycine betaine.

SUMMARY OF THE INVENTION

The present invention provides methods and compositions for slowing or controlling the timing of the ripening, maturation, senescence, abscission or preventing pathogen entry of produce, for example, fruit, vegetables, ornamental plants, etc. The methods involve the application of a photosynthetic pigment or membrane stabilizing agent such as glycine betaine to the produce pre- or post-harvest (or both), thereby lengthening the time period during which the produce can be transported and stored before being made available to consumers. The delay in ripening or maturation is advantageously reversible: with the passage of time, the effects of e.g. glycine betaine decrease, and ripening occurs. The methods are especially useful for treating produce that does not respond well to the application of 1-MCP, e.g. pears. However, the application of the stabilizing agent may be used for any and all produce in place of or in conjunction with 1-MCP or other agents, in order to modulate or control the ripening and/or maturation processes, and to temporarily prevent or slow the onset of senescence.

The practice of the invention will advantageously impact the produce (e.g. fruit and vegetable) industry in at least the following ways:

1) The use of the invention allows for the regulation of ripening so that the maturation process of produce is controlled and/or delayed e.g. senescence is delayed, and reduced amounts of soluble solids are maintained;

2) The use of the invention decreases the incidence of fruit drop, or organ abscission, enabling a longer growing season or delaying harvest time;

3) The use of the invention as described herein to reduce incidence of preharvest, at harvest, or postharvest pathogen entry from bacteria, fungi, or other pathogens of produce.

4) The use of the invention provides an alternative to 1-MCP and the effects of glycine betaine, unlike 1-MCP, are reversible;

5) The use of the invention decreases rates of damage during shipment of e.g. pears and/or other commodities due to the preservation or maintenance of increased firmness after application;

6) Organic preparations can be formulated, which is not possible with 1-MCP in certain cases; and 7) The use of glycine betaine as described herein in combination with e.g. low levels of 1-MCP or other products that interfere with ethylene-related or unrelated ripening processes advantageously allows for a synergistic slowing of ripening via multiple mechanisms. Suitable ratios of glycine betaine to another product in a mixture may range from e.g. about 90:10 to 10:90, including e.g. 50:50; or from about 65:35 to 35:65; or from about 75:25 to 25:75, etc;

It is an object of this invention to provide a method of delaying or slowing the ripening, maturation, abscission, or senescence of produce, or preventing pathogen entry into produce. The method comprises the steps of 1) identifying produce for which delaying or slowing ripening, maturation, abscission, senescence, or pathogen entry is desirable, and 2) applying a photosynthetic stabilizing agent to said produce. In some embodiments of the invention, the photosynthetic stabilizing agent is glycine betaine. The produce comprises, for example, fruits, vegetables, and/or ornamental plants. In some cases, the produce is a pear such as a d'Anjou pear. The step of applying may be carried out at one or more of before harvest, at harvest, or after harvest. Alternatively, or in addition, the step of applying may be carried out during shipping. Application may be by spraying, fogging, dipping, or by infiltration. The step of applying may utilize specific concentrations of photosynthetic stabilizing and requires human intervention, e.g. human intervention in one or more of the processes of ripening, maturation, abscission, and/or senescence of produce, and/or preventing pathogen entry into produce.

The invention also provides a method of delaying or slowing the ripening, maturation, abscission or senescence of and preventing pathogen entry into pears. The method comprises the steps of 1) identifying pears for which delaying or slowing ripening, maturation, abscission or senescence and preventing pathogen entry is desirable, and 2) applying a photosynthetic stabilizing agent to said pears. In some embodiments, the photosynthetic stabilizing agent is glycine betaine.

The invention further encompasses a composition comprising 1) glycine betaine, 2) 1-methylcyclopropene (1-MCP), and 3) a carrier suitable for application to produce. The invention further encompasses a composition comprising) glycine betaine, 2), aminoethoxyvinylglycine HCl, and 3) a carrier suitable for application to produce. The invention further encompasses a composition comprising 1) glycine betaine, 2), 1-naphthaleneacetic acid, and 3) a carrier suitable for application to produce.

DETAILED DESCRIPTION

The present invention provides methods and compositions that temporarily prevents or delays one or more of the ripening, maturation, abscission and senescence of, and/or prevention of pathogen entry into, produce such as fruits and vegetables. Further, the methods and compositions preserve the freshness of ornamental plants. The compositions comprise a photosynthetic membrane and/or pigment stabilizing agent such as glycine betaine, a natural product found in most fruit, vegetable and animal species. Without being bound by theory, it is believed that the external application of such an agent to produce that is not yet ripe or which is in the process of ripening slows the breakdown of photosynthetic pigment, which usually accompanies and/or participates in the ripening process. As a result of the slowing of photosynthetic membrane and/or pigment and protein complex breakdown, ripening or maturation of the produce is also slowed. However, the effect is not permanent. With time, the effects of the application decrease or reverse, and ripening/abscission/senescence/maturation proceeds in a normal manner. The application of e.g. glycine betaine thus reversibly prolongs the firmness of produce and retards the conversion of starches to soluble sugars, both of which are considered in the art to be indicators of ripening. The use of such an agent is particularly advantageous for use with e.g. pears, which can be problematic since they often fail to ripen at all (or only minimally) after exposure to conventional agents such as 1-MCP. The prolongation of ripening and/or maturation and/or the delay of abscission and/or the delay of senescence facilitates storage and transportation of produce, both with respect to time (i.e. the time of storage can be extended without loss due to spoilage), and with respect to decreasing damage that otherwise occurs during shipping and handling of softened, softening or wilting produce. Additionally, stabilization of membranes promotes the ability of the produce to withstand infection by pathogens.

By "prevention of pathogen entry" or "prevention of pathogen entry into" we mean that the use of glycine betaine slows or prevents or lessens the amount or extent of pathogen invasion or infestation of the plant or produce, compared to corresponding plants/plant tissue that is/are exposed to the pathogen under comparable conditions but without treatment with glycine betaine. Such invasion or infection may be, for example, actual entry of the pathogen (e.g. by boring, chewing, enzyme secretion, etc.) into plant tissue; or the eating of plant tissue at or near the surface; or the insertion of body parts of the pathogen into plant tissue (e.g. feeding or reproductive appendages); or the placement of reproductive means (e.g. the laying of eggs) in or on plant tissue; or the establishment of a colony in or on the plant or plant tissue, etc. Pathogens, pests and parasites that may be prevented from infecting plants, produce, etc. by the use of glycine betaine include but are not limited to: various rusts and blights; insects; nemartodes; fungi, bacteria, viruses, mildews, aphids, etc.

In one embodiment, the photosynthetic stabilizing agent is glycine betaine. While much of the discussion herein refers to glycine betaine, the discussion can apply equally to other photosynthetic stabilizing agents or precursors of glycine betaine such as choline or betainealdehyde, examples of which include but are not limited to: chlorophyllase inhibitors such as diisopropyl fluorophosphates, thylakoid membrane stabilizers such as spermine and 1,3-diaminopropane etc.

Glycine betaine (also known as betaine, trimethylglycine or "TMG", betaine anhydrous, N,N,N-trimethylglycine, etc.) is a natural compound that occurs in plants and animals as either glycine betaine or a choline-containing glycine betaine compound which can be enzymatically cleaved to form glycine betaine. First discovered in sugar beets, glycine betaine is produced abundantly as a byproduct of the manufacture of e.g. molasses and sugar from sugar beets and sugar cane. Significantly, this substance is known to be non-toxic and thus its use on comestible substances is safe with respect to consumption by humans or other animals. Betaine is already known for use as an animal feed supplement; in products for skin, hair and oral care (e.g. as a moisturizer and protectant); as a de-icing agent; as a sports performance enhancing agent that is added to e.g. sports drinks; and for other purposes. It is thus readily available commercially, for example, from Finnfeeds Finland, in Naantali, Finland, as the product BLUESTIM® (97% solution of betaine), and in various forms from the Danisco company; or as "Glycine Betaine" from Sunwin in China; or as "Prostim" "GREENSTIM®" or "Jinsaeng" from Agrogenesis in Finland (see, for example the websites located at www.agro-genesis.com/product_environmentalcare_turf.htmland and the website located at www.agro-genesis.com/product_cropscience_phyto.html; etc.

The glycine betaine that is used as described herein may be "organic", by which we mean that the source of the glycine betaine can be produced using methods that do not involve synthetic inputs such as synthetic pesticides, chemical fertilizers, etc. and, optionally, are not genetically modified or processed using irradiation, industrial solvents, or chemical food additives. Various standards of "organic" have been established in many countries and locations, including the United States, European countries, South American countries, and others. These standards may vary somewhat from location to location, but in general the definition provided above is what is intended when the term is used herein.

With respect to its use on produce as described herein, glycine betaine may be applied "as is" from a commercial source, or may be formulated or reformulated into a preparation that is used for application. Glycine betaine may be applied, for example, as a liquid solution that contains, e.g. at least about 10, 20, 30, 40, 50, 60, 70, 80, 90, or even about 100% glycine betaine, so long as the formulation is suitable for application, and so long as the applied solution adheres to or is retained at least partially on the surface of the produce or plant that is being treated. Further, glycine betaine is not always applied as a liquid; solid forms (e.g. crystals, dusts, aerosols, etc.) of this agent are also contemplated and encompassed by the invention, as are various gels or other forms. In addition, various substances that are not active (i.e. are inert) with respect to ripening in particular, or to produce in general, may be included in such formulations. For example, agents that aid in preparation or application of the formulation, or in retention of the glycine betaine on the produce after application, or for any other reason may be included, e.g. preservatives, colorants, detergents, various emulsifiers, diluents, buffering agents, salts, oils, lipids, waxes, solvents, penetrants, paper wrappings, packaging, storage boxes. Glycine betaine may also be directly infiltrated via vacuum or injected to retard ripening.

In addition, glycine betaine may be used alone or in combination with one or more other active agents which affect/improve/slow, etc. the ripening process, or which are beneficial to produce in some other way. By "used together" or "in combination" we mean that the two (or more, i.e. a plurality of) agents may be applied 1) separately one after the other within a relatively short period of time (e.g. simultaneously from separate preparations, or within minutes or hours, or the same day, or within a few days, etc.); or 2) the two or more agents may be mixed together into a single formulation that is applied. Glycine betaine may thus be used in combination with 1-MCP, other anti-ripening agents such as lysophosphatidylethanolamine; silver agents, aminoethoxyvinylglycine, aminooxyacetic acid, potassium permanganate (ethylene absorbent), aminoethoxyvinylglycine HCl, 1-naphthaleneacetic acid, etc. Additional active ingredients or additives that may be present in such compositions include but are not limited to: various antimicrobial substances; various antifungal agents; various insecticides; various pesticides; hormones, biotic applications, etc. For example, see U.S. Pat. Nos. 5,110,341; 6,177,072; and 7,150,884, the complete contents of each of which are hereby incorporated by reference, for a description of some exemplary ingredients or additives with which glycine betaine may be combined. Generally, the amount of glycine betaine in such a composition is from about 1 to about 99%.

Those of skill in the art will recognize that the amount of glycine betaine that is applied may vary from circumstance to circumstance, e.g. according to the produce that is being treated, according to the desired amount of delay that is desired, according to the environment during delivery (e.g. in an orchard vs in a shipping container), according to weather conditions, etc. In general, the amount for application "in the field" e.g. in an orchard, filed, etc. is from about 0.5 to about 50, or from about 1 to about 15, or from about 2.5 to 10, e.g. about 1, 2, 3, 4, 5, 6, 7, 8, 9, 10, 11, 12, 13, 14, 15, 16, 17, 18 19, 20, 25, 30, 35, 40, 45 or 50 pounds per acre. For other scenarios, such as in shipping containers, about 20, 40, 60, 80 or 100 pounds is applied.

According to the invention, glycine betaine may be applied to any type of produce, (including fruit, vegetables, and ornamental plants) for which it is desirable to slow maturation. Thus, the term "produce" as used herein is intended to be interpreted broadly, and to include plant-based agricultural products that are typically referred to as fruits, vegetables, grasses, grains, ornamental plants, bulbs, nuts, etc.

With respect to fruit, those of skill in the art will recognize that the word "fruit" may have a variety of meanings. For example, standard definitions include: 1. edible part of plant: an edible part of a plant, usually fleshy and containing seeds; 2. ovary of a plant: the ripened seed-bearing ovary of a plant; and 3. produce: the produce of any plant grown or harvested by humans. In broad terms, "fruit" may refer to a structure of a plant that contains its seeds. In non-technical usage, such as food preparation, "fruit" may refer to the fleshy seed-associated structures of certain plants that are sweet and edible in the raw state, such as apples, oranges, grapes, strawberries, juniper berries, bananas, etc., although non-sweet or less sweet fleshy structures (e.g. root vegetables such as carrots, beets, sweet potatoes, yams, etc.) are also included. Seed-associated structures that do not fit these informal criteria may be referred to by other names, such as vegetables, pods, ears, etc. In the botany of flowering plants, a "fruit" is a part that derives from specific tissues of the flower, mainly one or more ovaries. Taken strictly, this definition excludes many structures that are "fruits" in the common sense of the term, while including many structures that are not commonly called "fruits", such as bean or pea pods, corn kernels, tomatoes, etc. all of which are encompassed by the present invention.

Many fruits that, in a botanical sense, are true fruits are actually treated as vegetables in cooking and food preparation, including cucurbits (e.g., squash, pumpkin, gourds, melons, cucumbers, etc.), tomatoes, peas, beans, corn, eggplant, and sweet pepper, as wells as some spices, such as allspice and chilies.

As used herein, the term "fruit" refers to all plant products encompassed by the botanical, culinary and common meanings of the word.

Exemplary types of fleshy, simple fruits encompassed by the invention include but are not limited to: stone fruit or drupe (e.g. plum, cherry, peach, apricot, olive, mango, etc.); pome fruits of the family Rosaceae, (including apples, pears, rosehips, saskatoon berry, etc.); aggregate fruits such as achenes (e.g. strawberry), follicles, drupelets (raspberry and blackberry), and various other berries; multiple fruits such as pineapple, fig, mulberry, osage-orange, breadfruit, hedge apple, etc; citrus fruits such as oranges, lemons limes, grapefruits, kumquats, tangelos, ugli fruit, tangerines, tangelos, minnolas, etc.; so-called "true" berries such as black current, red current, gooseberry, tomato, eggplant, guava, lucuma, chilis, pomegranates, kiwi fruit, grape, cranberry, blueberry, etc.; including both seeded and seedless varieties, as well as hybrid and genetically altered or manipulated varieties; and others such a avocados, persimmons, etc.

In one embodiment of the invention, the fruit that is treated using the methods and compositions of the invention is a pear. By "pear" we mean the fruit of a member of the genes *Pyrus*, examples of which include but are not limited to *Pyrus amygdaliformis* (Almond-leafed pear); *Pyrus armeniacifolia*; *Pyrus boissieriana*; *Pyrus bourgaeana* (Iberian pear); *Pyrus×bretschneideri* (Chinese white pear; also classified as a subspecies of *Pyrus pyrifolia*); *Pyrus calleryana* (Callery pear); *Pyrus communis* (European pear); *Pyrus communis* subsp. *communis* (European pear cultivars of which include Beurre d'Anjou, Bartlett and Beurre Bose); *Pyrus communis* subsp. *caucasica* (syn. *P. caucasica*); *Pyrus communis* subsp. *pyraster* (wild European pear (syn. *Pyrus pyraster*); *Pyrus cordata* (Plymouth pear); *Pyrus cossonii* (Algerian pear); *Pyrus dimorphophylla*; *Pyrus elaeagnifolia* (oleaster-leafed pear); *Pyrus fauriei*; *Pyrus gharbiana*; *Pyrus glabra*; *Pyrus hondoensis*; *Pyrus koehnei* (evergreen pear of southern China and Taiwan); *Pyrus korshinskyi*; *Pyrus mamorensis*; *Pyrus nivalis* (snow pear); *Pyrus pashia* (Afghan pear); *Pyrus× phaeocarpa*; *Pyrus pseudopashia*; *Pyrus pyrifolia* (Nashi pear, Sha Li); *Pyrus regelii*; *Pyrus salicifolia* (willow-leafed pear); *Pyrus×serrulata*; *Pyrus×sinkiangensis* (thought to be an interspecific hybrid between *P.×bretschneideri* and *Pyrus communis*); *Pyrus syriaca*; *Pyrus ussuriensis* (Siberian pear) and *Pyrus xerophila*.

Major types of pears which are marketed and which may be treated by the methods and compositions of the invention include but are not limited to: Williams' Bon Chrétien (sold in the United States. as Bartlett), Red Bartlett varieties, d'Anjou, Bosc, Cornice, Abate Fatelle, Concorde, and Seckel pears.

Glycine betaine may also be used to slow the development, ripening, maturation, abscission, or onset or progression of senescence of, or to prevent pathogen entry into, vegetables. As used herein, the term "vegetable" refers to an edible plant or part of a plant, and typically means the leaf, stem, or root of a plant but also includes some "fruits" as well (such as squash, see above). The meaning of this word is largely based on culinary and cultural tradition and all common meanings that are recognized by those of skill in the art are encompassed herein. Vegetables may be categorized as allium, brassica or cruciferous, composite, gourds, umbelliferous, amaranth, grass, morning glory, nightshade, legumes, root, leafy green, etc. and all such vegetables may be treated using the methods and compositions of the invention.

Glycine betaine may also be used to slow the development, maturation, abscission, or senescence of, or prevent pathogen entry into, ornamental plants and hence to preserve their freshness. As used herein, the phrase "ornamental plant" refers to plants that are grown for decorative purposes such as e.g., house plants, those grown for cut flowers, etc. as well as certain grasses, annuals, perennials, shrubs, trees, etc. As used herein the phrase has the same meaning that it is generally used in the horticultural trades.

The application of glycine betaine to produce or plants may be carried out at any time at which it is desired to delay the onset and/or the progression of development, ripening, maturation, abscission, pathogen entry etc. In addition, various life stages of plants may be treated, e.g. sprouts, shoots or seedlings, etc. The methods of the invention involve identifying produce for which a delay in ripening, maturation, abscission, senescence, or pathogen entry is desired or suitable, and treating the produce as described herein. Accordingly, when treating produce, the produce may still be on the tree (or other plant from which it develops and grows), or may have already been harvested. The produce may be in any "stage" of ripening or maturation. For example, the produce (e.g. after harvest in the orchard, after harvest and when packed in a shipping container, etc.) may have characteristics of immature, "green" or "un-ripe" produce such as very low sugar content, high stringency, high "firmness", lack of colorful pigment, undeveloped or developing buds that have not bloomed, etc. Alternatively, the produce may have begun to mature or ripen in that e.g. the sugar content has begun to increase, firmness has begun to dissipate, the size has increased, blooming or flowering has (at least partially) commenced, etc. but the process is not complete. In yet other embodiments, the produce may be approaching maturity, but the application of glycine betaine causes suspension of further progression of sugar increase, softening, etc. so that the produce is "arrested" in a ripened or mature state and spoilage and senescence is prevented or slowed or deferred. In short, glycine betaine may be applied to produce at a stage prior to the onset of degradation of photosynthetic pigments in order to delay further ripening or maturation of the produce. In addition, glycine betaine may be applied repeatedly to produce or plants in order to extend its effects over a longer period of time.

In one embodiment, the methods of the invention are carried out before a fruit is "ripe", i.e. before the fruit has a soluble solids content or "SSC" (which generally corresponds to sugar content) that is generally recognized in the art as suitable for a fruit of interest. Those of skill in the art will recognize that this number or range varies widely from fruit to fruit. Percent sugar content is typically measured, for example, in degrees Brix (symbol °Bx) which is the sugar content of an aqueous solution. One degree Brix is 1 gram of sucrose in 100 grams of solution and represents the strength of the solution as percentage by weight (% w/w) (strictly speaking, by mass). If the solution contains dissolved solids other than pure sucrose, then the °Bx is only approximate the dissolved solid content. Those of skill in the art will recognize that typical Brix values for fruit and vegetables to which glycine betaine is applied as described herein will vary widely depending on the type of fruit or vegetable, and will be able to readily able to determine suitable values.

SSC values may be determined by various means, for example, by refractometry, by using various visible/near infrared (Vis/NIR) transmittance techniques, etc.

In addition, the degree of firmness and/or lack thereof may be used as an indicator of ripeness. Fruit firmness is generally measured as $kg/cm^{-2}$ and suitable ranges of firmness values for unripened and ripe fruit and vegetables are well-known to those of skill in the art. Firmness may be measured using a variety of instruments such as various fruit firmness testers, force gauges, etc.

In addition, other criteria may also be employed to determine the extent of ripeness (or lack thereof) of a fruit, for example, color, aroma, free acids, starch content, internal ethylene, etc.

Those of skill in the art will recognize that all pieces of produce in a batch that is being analyzed for possible treatment according to the methods of the invention may not be at the same stage of ripening at the same time. Thus, when a term such a "un-ripened fruit" is used, it may be used in the collective sense in that, for example, most or a significant portion of the fruit in a batch of interest is not ripe, e.g. at least about 10, 20, 30, 40, 50, 60, 70, 80, 90, or possibly 100% of the fruit meets the criteria set forth herein as "not-ripened" or "partially" or "fully" ripened, etc. as the case may be. In addition, those of skill in the art will recognize that the criteria for determining the stage of ripeness or maturation may differ from produce type to produce type, or depending on the use or intended handling of the produce type. For example, some apples are considered "ripe" or "mature" or "ready to eat" or "ready to use" e.g. for cooking (at least by consumers) when they are still very firm (e.g. crisp) and tart, while other apples, or other fruits, are much sweeter and/or softer when they are "ready".

With respect to vegetables and ornamental plants, the same or similar procedures apply, i.e. glycine betaine may be applied at any stage of development at which it is desired to arrest further maturation and/or prevent senescence or spoilage of a plant or plant product. The criteria for maturation or "readiness" for vegetables and ornamental plants are known to those of skill in the art and may be used to determine suitable times or stages for application. For example, application may be pre-harvest when a plant is still in the field, or post-harvest during storage or shipment. Glycine betaine may be applied to leaves and/or to any other accessible part of a plant, e.g. to portions of a plant such as leaves, pea pods, ears of corn still in the husk, etc., or, post-harvest to roots, peas that have been removed from pods, corn that has been husked, etc., to name only a few illustrative examples.

In some embodiments, glycine betaine is applied, usually by commercial growers, as a liquid solution using methods that are known to those of skill in the art, e.g. using known spray apparatuses such as spray guns, various pressurized apparatuses, etc._; or may be applied as a "fog" or aerosol e.g. within a storage or shipping compartment; or by dipping or washing of the produce; or by any other suitable means. However, it is not necessary that liquid formulations be used. Glycine betaine may also be applied as granules or as a "dust" using application technologies that are known in the art. Such applications may or may not be timed to coincide with other conditions such a weather, e.g. application of granules or dusts may be carried out soon after a rain or after application of another liquid (e.g. a liquid pesticide) or during periods of high humidity, etc., so that the granules/dust will readily adhere to the fruit (and liquefy, at least to some extent) on the exterior of the fruit.

The application of glycine betaine may be carried out only once, or may be repeated as needed or desired to maintain a desired status of the produce. For example, an initial application may be followed by subsequent applications at intervals of several days, or weeks, or months, etc. as required to keep the produce in the desired state. In addition, the application of glycine betaine may be preceded, followed or alternated with the application of other agents such as other anti-ripening, or anti-maturation agents; or ripening or maturation agents may be applied to hasten the reversal of the effects of glycine betaine. In general, the effects of a single application of glycine have a duration as long as from about 5 to about 30 days, and may be as short as from about 1 to about 5 days.

In another embodiment of the invention, glycine betaine is applied to produce or crops prior to harvest while they are "in the field" (orchard, etc.) in order to protect the produce or crops from environmental stress such as drought, excessive heat, excessive cold, sun damage, etc. The application under these circumstances is essentially the same as described above, but the produce or crop is identified as being at risk of damage due to untoward environmental conditions such a weather, e.g. lack of rain, high temperatures, etc.

In another embodiment of the invention, glycine betaine is applied to produce or crops prior to harvest while they are "in the field" (orchard, etc.) in order to delay the abscission or fruit drop of the produce. This application may occur one or multiple times in a growing season.

In some embodiments of the invention, glycine betaine preparations are prepared essentially for use by commercial growers and/or entities which are involved in the storage or shipping of produce. However, in other embodiments, the formulations are marketed and sold directly to consumers, e.g. to a consumer who wishes to delay the ripening or spoilage of fruit. Due to the known safety of glycine betaine, provision of such preparations directly to consumers does not pose a health risk, even if, for example, directions supplied with the preparation are not followed precisely, or if a solution of glycine betaine is spilled, consumed by a pet, etc. For example, small-scale, sprayable liquid solutions may be provided, and/or concentrated solutions or granules which can be diluted or dissolved and applied by spraying or by other means (e.g. as a fruit "wash") may be provided. This option may be particularly appealing to consumers who like to buy produce ahead of time (e.g. to take advantage of a sale, to buy produce during peak season, etc.), and store it for a period of e.g. weeks or months, or who grow and harvest their own fruits, vegetables, flowers, etc.

In addition, "green" and/or "organic" and/or "environmentally sensitive" products comprising glycine betaine may be developed and marketed for use, for example, by growers, suppliers, consumers, etc., especially since glycine betaine is a natural by-product of other processes and thus its use can truly be deemed efficient, not wasteful, etc.

EXAMPLES

Example 1

Figure 1:
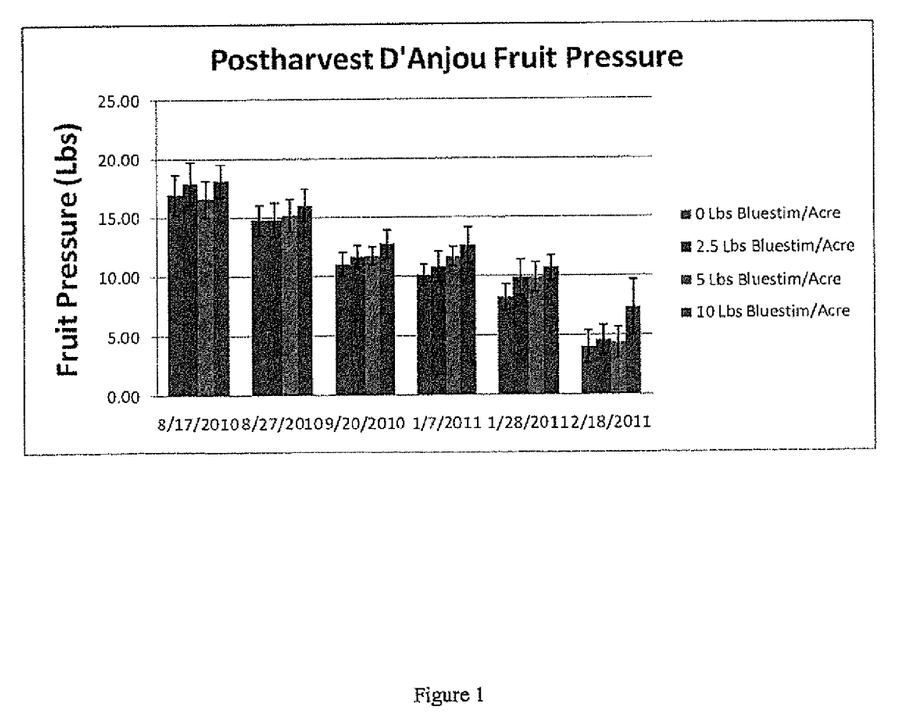
FIG. 1. Fruit pressure of Bluestim™ (glycine betaine)-treated and untreated d'Anjou pears. D'Anjou pears were treated on trees with Bluestim™ concentrations of 0, 2.5, 5, and 10 lbs/acre on Aug. 17, 2010. Pears were harvested on Sep. 20, 2010 and stored in commercial controlled atmosphere (CA) facilities. Pears were removed from storage on Jan. 7, 2011.
Figure 3:
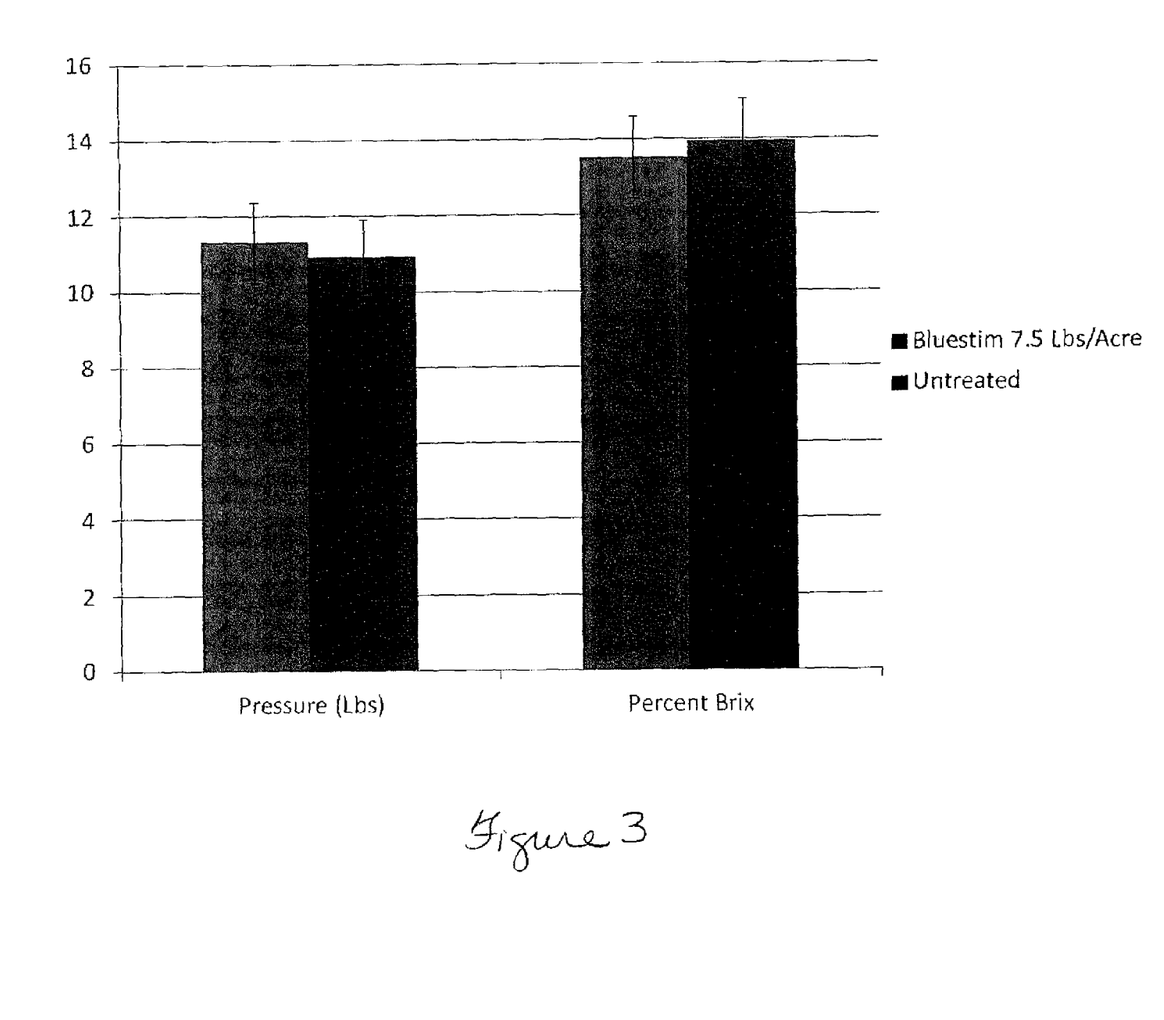
FIG. 3. Fruit pressure of Bluestim™ (glycine betaine)-treated and untreated d'Anjou pears. D'Anjou pears were treated on trees with Bluestim™ concentrations of 0 and 7.5 lbs/acre before harvest. Pears were harvested during the fall and stored in commercial controlled atmosphere (CA) facilities. Pears were removed from storage approximately 3 months later. Fruit firmness and % Brix were measured approximately 1 month after removal from storage.

Research described in this Example shows that application of a natural byproduct of molasses, glycine betaine, to d'Anjou pears before harvest yields firmer pears compared to untreated pears stored in the same post-harvest conditions (FIGS. 1 and 3). Application increased the fruit firmness in a dose dependent manner, with applications of 10 lbs/acre yielding the firmest pears.

Figure 2:
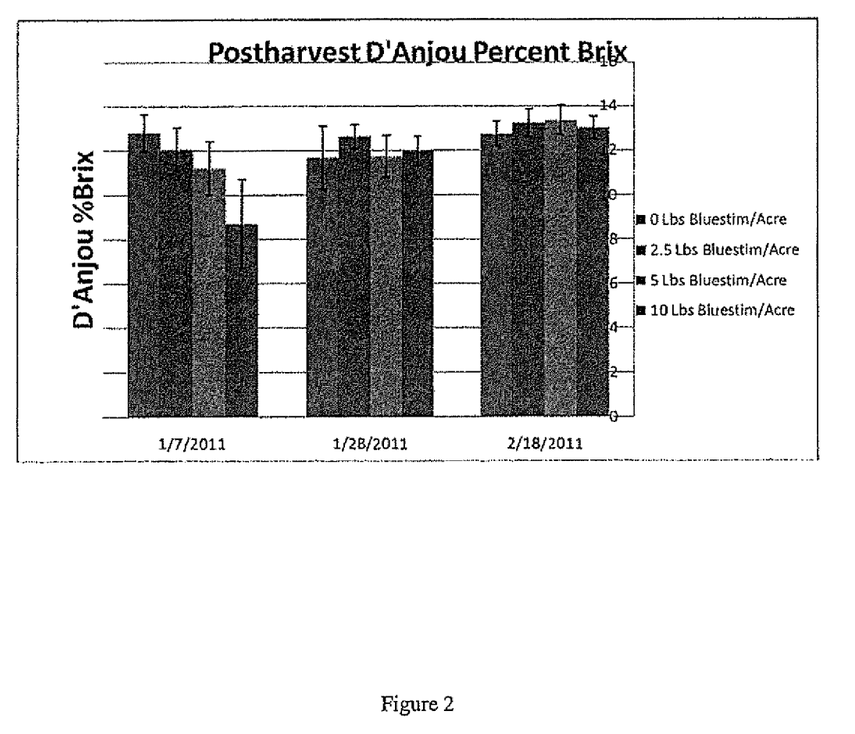
FIG. 2. Percent Brix of Bluestim™-treated pears after CA storage. Percent Brix were measured for all pear treatments after they were removed from the commercial CA storage conditions.

Glycine betaine treated pears also display a decrease in soluble sugars measured in % BRIX in a dose dependent manner (FIGS. 2 and 3). Both firmness and % BRIX are used as an indicator of fruit ripeness.

As time passes, however, glycine betaine treated pears soften and exhibit increases in % BRIX, indicating that the effect is temporary, and that ripening eventually occurs after treatment.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of delaying or slowing the ripening or maturation of pears, comprising the steps of
    identifying immature pears for which delaying or slowing ripening or maturation is desirable;
    applying glycine betaine to said pears, wherein said step of applying an effective amount of is carried out at or after harvest.

2. The method of claim 1 wherein said applying step includes applying an anti-ripening agent selected from the group consisting of 1-methylcyclopropene (1-MCP) and aminoethoxyvinylglycine HCl.

* * * * *

UNITED STATES PATENT AND TRADEMARK OFFICE
CERTIFICATE OF CORRECTION

PATENT NO. : 8,901,039 B2  
APPLICATION NO. : 13/826860  
DATED : December 2, 2014  
INVENTOR(S) : Amit Dhingra and Scott Schaeffer Page 1 of 1

It is certified that error appears in the above-identified patent and that said Letters Patent is hereby corrected as shown below:

In the Claims

Claim 1 in column 11, lines 14 to 20 should read as follows:

1. A method of delaying or slowing the ripening or maturation of pears, comprising the steps of
identifying immature pears for which delaying or slowing ripening or maturation is desirable;
applying an effective amount of glycine betaine to said pears, wherein said step of applying is carried out at or after harvest.

Signed and Sealed this  
Eleventh Day of August, 2015

Michelle K. Lee  
*Director of the United States Patent and Trademark Office*